United States Patent
Seleem

(10) Patent No.: US 10,301,664 B2
(45) Date of Patent: May 28, 2019

(54) REPURPOSING NON-ANTIMICROBIAL DRUGS AND CLINICAL MOLECULES TO TREAT BACTERIAL INFECTIONS

(71) Applicant: Purdue Research Foundation, West Lafayette, IN (US)

(72) Inventor: Mohamed Seleem, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 109 days.

(21) Appl. No.: 15/380,648

(22) Filed: Dec. 15, 2016

(65) Prior Publication Data

US 2017/0189556 A1 Jul. 6, 2017

Related U.S. Application Data

(60) Provisional application No. 62/273,631, filed on Dec. 31, 2015.

(51) Int. Cl.
| | |
|---|---|
| C12Q 1/18 | (2006.01) |
| A61K 31/41 | (2006.01) |
| A61K 31/7072 | (2006.01) |
| A61K 31/7135 | (2006.01) |
| A61K 31/7056 | (2006.01) |
| A61K 31/7048 | (2006.01) |
| A61K 31/496 | (2006.01) |
| A61K 31/7036 | (2006.01) |
| A61K 31/351 | (2006.01) |
| A61K 31/575 | (2006.01) |
| A61K 38/15 | (2006.01) |
| A61K 31/5377 | (2006.01) |
| A61K 31/439 | (2006.01) |
| A61K 38/14 | (2006.01) |

(52) U.S. Cl.
CPC .............. *C12Q 1/18* (2013.01); *A61K 31/351* (2013.01); *A61K 31/41* (2013.01); *A61K 31/439* (2013.01); *A61K 31/496* (2013.01); *A61K 31/5377* (2013.01); *A61K 31/575* (2013.01); *A61K 31/7036* (2013.01); *A61K 31/7048* (2013.01); *A61K 31/7056* (2013.01); *A61K 31/7072* (2013.01); *A61K 31/7135* (2013.01); *A61K 38/14* (2013.01); *A61K 38/15* (2013.01)

(58) Field of Classification Search
None
See application file for complete search history.

(56) References Cited

U.S. PATENT DOCUMENTS

| | | | | |
|---|---|---|---|---|
| 2013/0310346 A1* | 11/2013 | Zurawski | ............... | A61K 38/16 514/154 |
| 2017/0112877 A1* | 4/2017 | Huang | .................. | A61K 33/40 |

OTHER PUBLICATIONS

Thangamani et al (Scientific Reports 5:11596 13 pages). (Year: 2015).*

* cited by examiner

*Primary Examiner* — Christopher M Gross
(74) *Attorney, Agent, or Firm* — Purdue Research Foundation; Yonghao Hou

(57) ABSTRACT

Disclosed herewith is drug repurposing efforts that lead to the discovery of prior non-antibiotic drugs can be used in clinical applicable ranges to treat patients of bacterial infection. These repurposed drug can be used either alone or in combination with traditional antibiotic drugs to treat bacterial strains that may develop or already have developed drug resistance.

11 Claims, 13 Drawing Sheets

REPURPOSING NON-ANTIMICROBIAL DRUGS AND CLINICAL MOLECULES TO TREAT BACTERIAL INFECTIONS

CROSS REFERENCE

This application claims the benefits of U.S. Provisional Application 62/273,631 under 35 U.S.C. § 119 (e), which was filed on Dec. 31, 2015. The content of which is expressly incorporated entirely.

GOVERNMENT RIGHTS

This invention was made with government support under AI114861 awarded by the National Institutes of Health. The government has certain rights in the invention.

TECHNICAL FIELD

The present disclosure generally relates to drug repurposing, and in particular to use a list of identified FDA approved drugs as potent antimicrobial agents against gram-positive pathogens.

BACKGROUND

This section introduces aspects that may help facilitate a better understanding of the disclosure. Accordingly, these statements are to be read in this light and are not to be understood as admissions about what is or is not prior art.

Bacterial infections have become a serious threat to the global public health due to the dearth of effective antimicrobials. Moreover, the development of new antibiotics is becoming increasingly difficult and is unable to keep pace with the rapid emergence of resistant pathogens. Hence, novel drugs and new approaches to develop them are urgently needed. Both de novo drug discovery and drug repurposing have been used in the search for an effective antibiotic. Unlike the lengthy and costly process of de novo drug discovery, drug repurposing can reduce the time, cost and risk associated with drug innovation. Drug repurposing has already resulted in successes in a number of disease areas, including infectious diseases. Though antibiotics have been repurposed for other clinical indications, to date, not a single non-antibiotic drug has been repurposed for use as an antibacterial. Given the crucial problem posed by multidrug resistant pathogens, especially ESKAPE pathogens (*Enterococcus faecium, Staphylococcus aureus Klebsiella pneumoniae, Acinetobacter baumannii, Pseudomonas aeruginosa,* and *Enterobacter* spp), there is an unmet need for methods for drug repurposing to facilitate uncovering new treatment options.

SUMMARY

This disclosure provides a method of using newly identified FDA approved non-antibiotic drugs to treat bacterial infections in clinical relevant range. Particularly, a library containing hundreds of FDA approved non-antibiotic drugs are screened both in vitro and in vivo to identify drugs that are in clinically relevant range to kill bacterial pathogens. These pathogens include multi-drug resistant strains *Enterococcus faecium, Staphylococcus aureus Klebsiella pneumoniae, Acinetobacter baumannii, Pseudomonas aeruginosa,* and *Enterobacter* spp. (ESKAPE). Presented herewith are Ebselen, Auranofin and FdUrd possess potent antimicrobial effects in clinical applicable range on MRSA infected mice.

The antibacterial activity of these drugs are tested via various methods including but not limited to biofilm mass reduction, bacteria toxin production associated inflammatory cascades, mitochondrial protein synthesis and macromolecular synthesis. The clinical applicable range of these drugs may be about sub-micromolar to about nanomolar according to the in vitro and in vivo test results, and they are well within the scope of clinically achievable concentration in a patient.

This disclosure further provides a combinational therapy to a patient with bacterial infection to control/prevent the development of drug-resistance. The combinational therapy may comprise applying a clinical range of aforementioned non-antibiotic drug with a conventional antibiotic drug to the patient. The non-antibiotic drug may be selected from the group consisting of Ebselen, Auronaufin and 5-fluoro-2'-deoxyuridine (FdUrd), and the conventional antibiotic drug is selected from the group consisting of linezolid, clindamycin, vancomycin, ciprofloxacin, erythromycin, rifampicin, gentamicin, mupiocin, fusidic acid, retapamulin and daptomycin.

In some embodiment, the aforementioned non-antibiotic drug provides synergy to the selective conventional antibiotic drug in the combinational therapy and prolongs each drug's clinical utility life span.

In some embodiment, the aforementioned non-antibiotic drug kills invasive bacteria that become intracellular.

In some embodiment, the aforementioned non-antibiotic drug provides bactericidal effects to bacteria that already developed resistance to an existing drug.

In some embodiment, the aforementioned non-antibiotic drug reduces the production of inflammatory cytokines induced by MRSA skin infection.

It is conceivable that through the study of these drugs' mode of action on bacteria, more FDA approved drugs may be identified to have clinical relevance to treat multi-drug resistant bacteria.

These and other features, aspects and advantages of the present invention will become better understood with reference to the following figures, associated descriptions and claims.

DETAILED DESCRIPTION

Figure 1:
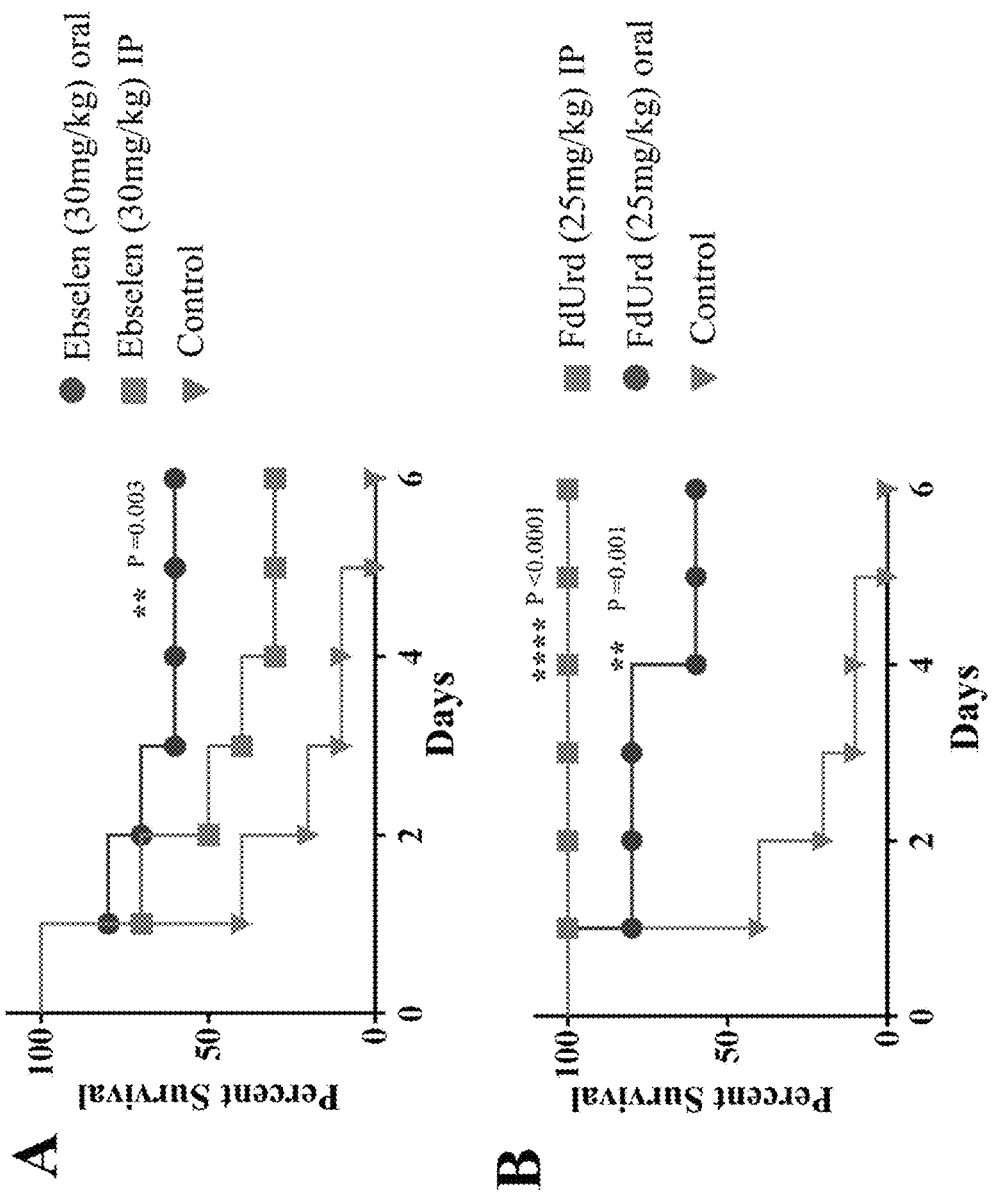
FIG. 1A shows the efficacy of treatment of MRSA septicemic infection with ebselen. Mice received one treatment daily for three days. Mice were monitored for six days and the cumulative percent survival was determined. The data were subjected to statistical analysis using Kaplan-Meier survival curves. A log rank test was performed for 95% confidence intervals by GraphPad Prism 6.0.
FIG. 1B shows the efficacy of treatment of MRSA septicemic infection with FdUrd. Mice received one treatment daily for three days. Mice were monitored for six days and the cumulative percent survival was determined. The data were subjected to statistical analysis using Kaplan-Meier survival curves. A log rank test was performed for 95% confidence intervals by GraphPad Prism 6.0.

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

Unless defined otherwise, the scientific and technology nomenclatures have the same meaning as commonly understood by a person in the ordinary skill in the art pertaining to this disclosure. For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Infections caused by Gram-positive drug-resistant pathogens are still a leading cause of mortality. Three species—methicillin-resistant *Staphylococcus aureus* (MRSA), Streptococcus pneumoniae and vancomycin-resistant enterococcus (VRE)—are responsible annually for at least 84% of the antibiotic-resistant bacteria mortality in the United States alone.

Drug development is a time-consuming, costly, and high-risk venture given few compounds successfully make it through stringent regulatory requirements to the marketplace. Collectively, this points to a critical need for the identification of novel strategies to develop antibiotics to deal with this challenging health issue. One strategy which warrants more attention for identifying new antimicrobials is drug repurposing. Repurposing existing approved drugs permits companies to bypass much of the preclinical work and early stage clinical trials required for new compounds thus cutting into the cost associated with bringing a drug to the marketplace.

In response to the pressing need to develop novel antimicrobials to circumvent the scourge of antimicrobial resistance, drug-repurposing efforts are deployed to identify non-antibiotic drugs exhibiting bactericidal activity and they have gained some ground; however, these identified drugs possess high minimum inhibitory concentration (MIC) values that cannot be achieved clinically. For the purpose of this disclosure, a MIC within clinical achievable range is deemed as clinical applicable range to kill the bacterium at issue. Depending on the strain of the bacterium and the FDA-approved drug being investigated, this clinical applicable range may be about sub-micromolar to about nanomolar.

This high MIC value is a major impediment to repurposing these drugs as antimicrobial agents. The objective of this disclosure is to identify non-antibiotic drugs with potent antimicrobial activity within an applicable clinical range. This is done by first screening FDA approved drug library to identify groups of drugs that show antimicrobial effect as hit compounds. Then using the hit compounds with their clinical applicable range to test their in vitro and/or in vivo effect on several multi-drug resistant pathogens, for example, methicillin-resistant *S. aureus* (MRSA), vancomycin-resistant *S. aureus* (VRSA), and vancomycin-intermediate *S. aureus* (VISA).

A library, containing 727 FDA approved drugs and small molecules, was screened against ESKAPE pathogens (*Enterococcus faecium, Staphylococcus aureus, Klebsiella pneumoniae, Acinetobacter baumannii, Pseudomonas aeruginosa*, and *Enterobacter cloacae*). Drugs that showed antimicrobial activity in an applicable clinical range were further tested in vitro and in vivo in an infected mouse model. The initial screening identified 24 non-antibiotic drugs and clinical molecules active against Gram-positive pathogens including methicillin-resistant *S. aureus* (MRSA) and vancomycin-resistant *enterococcus* (VRE) isolates. Two non-antibiotic drugs showed activity against Gram-negative pathogens. Among the active non-antibiotic drugs, ebselen (EB) and 5-fluoro-2'-deoxyuridine (FdUrd), showed bactericidal activity, in an applicable clinical range, against multi-drug-resistant *Staphylococcus* isolates including MRSA, vancomycin-resistant *S. aureus* (VRSA), and vancomycin-intermediate *S. aureus* (VISA). The minimum inhibitory concentration at which 90% of clinical isolates of *S. aureus* were inhibited ($MIC_{90}$) was found to be 0.25 and 0.0039 mg/L for EB and FdUrd, respectively. Treatment with EB orally significantly increased mice survival in a lethal model of septicemic MRSA-infection by (60%) compared to that of control. FdUrd oral and intraperitoneal treatment significantly enhanced mouse survival by 60% and 100%, respectively, in a lethal model of septicemic MRSA-infection compared to that of control. These data encourage screening and repurposing of non-antibiotic drugs and clinical molecules to treat multidrug-resistant bacterial infections.

In an intensive search and subsequent study for antimicrobial activity in an applicable clinical range among non-antimicrobial drugs, at least three drugs, ebselen (EB), Auranofin, and 5-fluoro-2'-deoxyuridine (FdUrd), have been identified with potent antibacterial activities against Gram-positive pathogens, including highly multidrug-resistant clinical isolates of *S. aureus*, with MIC values in an applicable clinical range. These drugs showed antibacterial activity against clinical isolates of methicillin-resistant *S. aureus* (MRSA), vancomycin-resistant *S. aureus* (VRSA), and vancomycin-intermediate *S. aureus* (VISA) with MIC values in submicromolar concentrations. Additionally, at least some of these drugs showed significant levels of protection against a lethal model of septicemic MRSA-infection in mice. It should be appreciated that while the present disclosure focuses on identifying non-antibiotic drugs with potent antimicrobial activity, such reference is not intended to be limiting in nature, as the methods described herein can also be applied to identifying non-antibiotic drugs with potent antifungal activity and anti-anthrax activity.

Repurposing drugs, with well-characterized toxicology and pharmacology, to find new applications outside the scope of the original medical indication is a novel way to reduce both the time and cost associated with antimicrobial innovation. These identified FDA approved drugs can be applied to infected patient for 1) killing intracellular and persistent MRSA, 2) disrupting adherent staphylococcal biofilms, 3) suppressing toxin production and key virulence factors, 4) reducing excessive host-inflammatory responses associated with these toxins, 5) significantly reducing both the bacterial load and levels of the pro-inflammatory cytokines in MRSA skin lesions, and 6) enhancing wound healing. In addition, these drugs have many advantageous qualities including; a) they are FDA-approved and clinically safe molecules, b) orally bioavailable, c) possess potent bactericidal activity in a clinically achievable range, d) exhibit very low frequency of bacterial resistance, e) demonstrate a synergistic activity with conventional antibiotics, and f) possess a novel mechanism of action.

To date, no FDA-approved drug has been repurposed to treat bacterial infections in clinical relevant range. The non-antibiotic drugs that showed antimicrobial activity serve as untapped reservoir for new antibiotic leads that could lead to identification of new targets which will guide the future development of improved antimicrobial agents. The library we screened represents only 7% of the total drugs known to clinical medicine. Finding hits in a clinical range illustrates the potential to identify more drugs with potent antimicrobial activity and encourage the screening of all clinical compounds to complement current antibiotics.

The disclosure herein further provides that repurposing auranofin and ebselen to treat bacterial infections has the potential to produce significant impact that leapfrog the drug development process and save years of expensive research. Both drugs has significant promise to be repurposed as a novel antibacterial for treatment of both superficial and invasive infections.

Auranofin is currently approved for long-term treatment of unresponsive rheumatoid arthritis. Auranofin's oral bioavailability and reduced associated side effects offer significant advantages over traditional injectable gold drugs. The emergence of new anti-rheumatoid drugs with fewer side effects and faster activity has resulted in the decline of oral gold therapy clinically. Nevertheless, there has been considerable research efforts employed to identify alternative therapeutic applications for auranofin, particularly in the area of infectious diseases. The fact that auranofin, a FDA-approved gold compound used for treating rheumatoid arthritis, recently has been granted orphan-drug status from the FDA for treatment of human amebiasis, further validates the herein disclosed antimicrobial repurposing approach for Auranofin.

Materials and Methods:
Bacterial Strains:
ESKAPE pathogens vancomycin resistant *E. faecium* ATCC 700221 (VRE), MRSA USA300, carbapenemase (KPC)-producing $bla_{KPC+}$ *K. pneumoniae* ATCC BAA-1705, multi-drug-resistant *A. baumannii* ATCC BAA-1605, *P. aeruginosa* ATCC 15442, and *E. cloacae* ATCC BAA-1143 were used for the initial screening. Clinical isolates of methicillin-sensitive *S. aureus* (MSSA), MRSA, VRSA, VISA, and *S. epidermidis* are described in Table 1.

Compounds and Library:
The NIH Clinical Collections 1 and 2 (http://www.nih-clinicalcollection.com) containing 727 FDA approved drugs and small molecules previously used in human clinical trials with known safety profiles were screened against ESKAPE pathogens. The library was initially screened at a single concentration of 16 µM to identify "hit" non-antibacterial drugs. Once the antimicrobial activity of the drugs was confirmed, we determined their MICs and minimum bactericidal concentrations (MBCs) according to the Clinical and Laboratory Standards Institute (CLSI). Drugs were selected that showed potent antimicrobial activity in an applicable clinical range for further screening and testing in vitro and in vivo in an infected mouse model.

Animals:
Animal procedures were approved by the Purdue University Animal Care and Use Committee (PACUC) (protocol no. 1311000988). Eight-week-old female BALB/c mice (Harlan Laboratories, Indianapolis, Ind.) were used for this study. Mice were rendered neutropenic by treatment with cyclophosphamide intraperitoneally (IP) 150 and 100 mg/kg at four days and one day before infection, respectively. Neutropenic mice were inoculated IP with $8 \times 10^8$ MRSA USA200. At one hour after infection, the mice were divided into five groups (n=10 per group), and two groups were treated orally with either EB 30 mg/kg or FdUrd 25 mg/kg. Two groups were treated IP with either EB 30 mg/kg or FdUrd 25 mg/kg. One group was used as a control with no treatment. Treatment was continued once daily for two more days (animals received three doses total). Mortality was monitored four times daily for six days, and the cumulative percent survival was determined. The data were subjected to statistical analysis using Kaplan-Meier survival curves. A log rank test was performed for 95% confidence intervals by GraphPad Prism 6.0 (GraphPad Software, La Jolla, Calif.).

Example 1. In Vitro Antimicrobial Activity from Screening of FDA-Approved Drug Library In this Example, we identified and validated drugs that are active against Gram-positive pathogens MRSA and VRE in clinical relevant range.

Initial screening identified 24 non-antibiotic drugs and clinical molecules active against Gram-positive pathogens MRSA and VRE (Table 2). Among the active non-antimicrobial drugs against MRSA identified in the NIH Clinical Collections, EB and FdUrd showed potent bactericidal activity in a nano-molar (clinically achievable) range. Both drugs demonstrated potent bactericidal activity against clinical multi-drug-resistant *Staphylococcus* isolates. The MIC at which 90% of *S. aureus* isolates were inhibited ($MIC_{90}$) was found to be 0.25 and 0.0039 mg/L for EB and FdUrd, respectively (Table 1). Only two non-antibiotic drugs showed activity against Gram-negative pathogens (Table 2).

TABLE 1

The MIC and MBC of Ebselen and FdUrd against Gram-positive Pathogens

| Strains type | Strain ID | Isolation Origin | year | Phenotypic properties | MIC/MBC (mg/L) Ebselen | FdUrd |
|---|---|---|---|---|---|---|
| Vancomycin-resistant *S. aureus* (VRSA) | VRSA1 | United States | 2002 | Resistant to erythromycin and spectinomycin as well as being multiresistant to other commonly used therapeutic agents | 0.25/0.25 | 0.0078/0.0078 |
| | VRSA2 | United States | 2002 | Resistant to erythromycin and spectinomycin as well as being multiresistant to other commonly used therapeutic agents | 0.25/0.25 | 0.0039/0.0156 |
| | VRSA3a | United States | 2004 | Resistance to tetracycline, macrolides, lincosamides and aminoglycoside | 0.25/0.25 | 0.000975/0.000975 |
| | VRSA3b | United States | — | — | 0.25/1 | 0.00049/0.00049 |
| | VRSA4 | United States | 2005 | Resistant to erythromycin and spectinomycin | 0.125/0.125 | 0.00195/0.0039 |
| | VRSA5 | United States | 2005 | Resistant to erythromycin and spectinomycin | 0.25/0.25 | 0.00195/0.00195 |
| | VRSA6 | United States | — | Resistant to vancomycin | 0.25/0.5 | 0.00049/0.00195 |
| | VRSA7 | United States | 2006 | Resistant to β-lactams, erythromycin and spectinomycin | 0.5/0.5 | 0.00195/0.0039 |
| | VRSA8 | United States | 2007 | Resistant to erythromycin and spectinomycin | 0.125/0.125 | 0.00049/0.000975 |
| | VRSA9 | United States | 2007 | Resistant to erythromycin and spectinomycin | 0.25/0.5 | 0.000975/0.00195 |
| | VRSA10 | United States (Michigan) | 2009 | Resistant to ciprofloxacin, clindamycin, erythromycin, gentamicin, and vancomycin | 0.25/0.25 | 0.000975/0.000975 |

TABLE 1-continued

The MIC and MBC of Ebselen and FdUrd against Gram-positive Pathogens

| Strains | | Isolation | | | MIC/MBC (mg/L) | |
|---|---|---|---|---|---|---|
| type | Strain ID | Origin | year | Phenotypic properties | Ebselen | FdUrd |
| | VRSA11a | United States | 2010 | Resistant to erythromycin and spectinomycin | 0.125/0.25 | 0.000975/0.0156 |
| | VRSA11b | United States | 2010 | Resistant to erythromycin and spectinomycin | 0.25/0.25 | 0.000975/0.0039 |
| | VRSA12 | United States | — | Resistant to vancomycin | 0.25/0.5 | 0.00195/0.0039 |
| | VRSA13 | United States | — | Resistant to vancomycin | 0.25/0.25 | 0.00195/0.0156 |
| Methicillin resistant S. aureus (MRSA) | NRS382 | United States (Ohio) | — | Resistant to ciprofloxacin, clindamycin, erythromycin, and methicillin | 0.125/0.125 | 0.000975/0.0078 |
| | NRS383 | United States (NorthCarolina | — | Resistant to ciprofloxacin, clindamycin, erythromycin, gentamicin, and methicillin | 0.125/0.125 | 0.0078/0.0078 |
| | NRS 384 | United States (Mississippi) | — | Resistant to erythromycin, methicillin, and tetracycline | 0.125/0.125 | 0.00195/0.00195 |
| | NRS 385 | United States (Connecticut) | — | Resistant to ciprofloxacin, clindamycin, erythromycin, gentamicin, methicillin, tetracycline, and trimethoprim | 0.5/1 | 0.0315/0.0315 |
| | NRS 386 | United States (Louisiana) | — | Resistant to erythromycin and methicillin | 0.125/1 | 0.00195/0.0078 |
| | NRS 387 | United States (Washington) | — | Resistant to methicillin | 0.125/0.25 | 0.0039/0.0156 |
| | NRS 483 | United States (Vermont) | — | Resistant to erythromycin and methicillin | 0.125/0.5 | 0.00195/0.0078 |
| | NRS 484 | United States (Alaska) | | Resistant to methicillin | 0.25/0.25 | 0.000975/0.0039 |
| | NRS70 | Japan | 1982 | Resistant to clindamycin, erythromycin and spectinomycin | 0.25/0.25 | 0.0039/0.00315 |
| | NRS71 | United Kingdom | — | Resistant to tetracycline and methicillin | 0.25/0.25 | 0.00195/0.00195 |
| | NRS100 | United Kingdom | — | Resistant to tetracycline | 0.25/0.5 | 0.000975/0.000975 |
| | NRS108 | France | — | Resistant to gentamicin | 0.25/0.25 | 0.0078/0.0156 |
| | NRS119 | United States (Massachuset) | 2001 | Resistant to linezolid | 0.125/0.25 | 0.0039/0.0156 |
| | NRS123 | United States | 1998 | Resistant to methicillin; susceptible to nonbeta-lactam antibiotics | 0.25/0.5 | 0.000975/0.0039 |
| | NRS194 | United States (North Dakota) | 1999 | Resistant to methicillin | 0.25/1 | 0.0039/0.0625 |
| Methicillin-sensitive S. aureus (MSSA | NRS72 | United Kingdom | — | Resistant to penicillin | 0.25/0.5 | 0.000975/0.00195 |
| | NRS77 | United Kingdom | 1960 | Used for typing phage 47 and is considered to be the original strain for most S. aureus genetic research. | 0.25/1 | 0.00049/0.00049 |
| | NRS846 | — | — | — | 0.125/>64 | 0.0039/0.0039 |
| | NRS860 | — | — | — | 0.25/0.25 | 0.00195/0.00195 |
| Vancomycin-intermediate S. aureus (VISA | NRS 1 | Japan | 1996 | Resistant to aminoglycosides and tetracycline (minocycline)Glycopeptide-intermediate S. aureus | 0.125/0.125 | 0.00195/0.00195 |
| | NRS19 | United States (Illinois) | 1999 | Glycopeptide-intermediate S. aureus | 0.25/0.025 | 0.00049/0.00195 |
| | NRS37 | France | 1995 | Glycopeptide-intermediate S. aureus | 0.125/0.125 | 0.00195/0.0078 |
| S. epidermidis | NRS 101 | United States | — | Prototype biofilm producer, Resistant to methicillin and gentamicin | 0.5/0.5 | 0.0078/0.0078 |
| Enterococcus species | E. fecalis ATCC 51229 (VRE) | Peritoneal fluid, St. Louis, MO | — | Low-level vancomycin-resistant, VanB Resistant to Vancomycin. Sensitive to Teichoplanin. | 0.5/0.5 | 0.125/0.125 |
| | E. faecium ATCC 700221 (VRE) | Human feces, Connecticut | — | Resistant to Vancomycin and Teicoplanin | 0.5/1 | 0.0625/0.125 |

TABLE 2

MIC and MBC of non-antibacterial drugs against Gram-positive and negative pathogens

| N | NCC structure | Name | Description | MIC/MBC µM MRSA | VRE |
|---|---|---|---|---|---|
| 1 | CPD000466308 | Epirubicin | Antineoplastic | 16/64 | 8 |
| 2 | CPD000469213 | Toremifene | Antineoplastic | 16/16 | 16 |
| 3 | CPD000058267 | Isoproterenol | Bronchodilator | 16/64 | >16 |
| 4 | CPD001491671 | Tamoxifen | Antineoplastic | 16/16 | >16 |
| 5 | CPD001317855 | Clomid | Treat infertility in women | 16/32 | 16 |
| 6 | CPD001906781 | Daunorubicin | Antineoplastic | 16/16 | 8 |
| 7 | CPD000469293 | Oxiconazole | Antifungal | 2/32 | >16 |
| 8 | CPD000466357 | Triclabendazole | Anthelmintic | 8/32 | >16 |
| 9 | CPD000466363 | Carmofur | Antineoplastic | 2/4 | >16 |
| 10 | CPD000466355 | Idarubicin | Antineoplastic | 4/4 | 4 |
| 11 | CPD000466278 | MK-886 | Leukotriene antagonist | 8/16 | 8 |
| 12 | CPD000058970 | Bifonazole | Antifungal | 8/>64 | >16 |
| 13 | CPD000058306 | Clotrimazole | Antifungal | 4/64 | >16 |
| 14 | CPD000466300 | 5-Nonyloxytryptamine | Serotonin receptor agonist | 4/8 | 8 |
| 15 | CPD000058445 | Ebselen | Mimic glutathione peroxidase | <0.5/0.5 | 0.5/1 |
| 16 | CPD001370749 | Econazole | Antifungal | 4/32 | >16 |
| 17 | CPD000058733 | Miconazole | Antifungal | 4/8 | >16 |
| 18 | CPD000038082 | 5-Fluorouracil | Antineoplastic | 4/16 | >16 |
| 19 | CPD001496941 | FdUrd | Antineoplastic | <0.5/0.5 | <0.5/0.5 |
| 20 | CPD000059106 | Ftorafur | Antineoplastic | >16 | 16 |
| 21 | CPD000469217 | Raltitrexed | Antineoplastic | >16 | 2 |
| 22 | CPD000469227 | Dactinomycin | Antineoplastic | >16 | 0.5 |
| 23 | CPD000058394 | Acetazolamide | Antiglaucoma | >16 | 1 |
| 24 | CPD000058202 | Furosemide | Diuretic | >16 | 4 |

| N | Drug | MIC/MBC µM K. pneumoniae | A. baumannii | E. cloacae | P. aeruginosa |
|---|---|---|---|---|---|
| 1 | 5-Nonyloxytryptamine | >16 | 16 | 16 | >16 |
| 2 | FdUrd | 8 | >16 | >16 | >16 |

Example 2. Protection of Mice Against MRSA Infection

In this Example, we showed that Ebselen provides protection of mice infected by MRSA.

EB oral treatment, but not IP, significantly increased mice survival (60%) compared to that of control (FIG. 1A). FdUrd oral and IP treatment significantly enhanced mouse survival by 60% and 100%, respectively, compared to that of control (FIG. 1B).

It is well established that currently approved antimicrobials are losing the battle in the fight against multidrug-resistant pathogens. Without a doubt, novel antimicrobials and novel approaches to develop them are urgently needed; however, new antimicrobials are becoming increasingly difficult to develop. Repurposing FDA-approved drugs, with well-characterized toxicology and pharmacology, to find new applications outside the scope of the original medical indication is a novel way to reduce both the time and cost associated with antimicrobial innovation.

Whole-cell screening assays of non-antibiotic drugs and clinical safe molecules in the NIH Clinical Collections against ESKAPE pathogens revealed several non-antibiotic drugs with antimicrobial activity (Table 2). Many drugs with antimicrobial activities were unexpected because their clinical indications are unrelated to treatment of microbial infections.

Among the active non-antimicrobial drugs against MRSA, EB and FdUrd showed potent bactericidal activity in a nano-molar (clinically achievable) range. Both drugs demonstrated potent bactericidal activity against clinical multi-drug-resistant Staphylococcus isolates, including linezolid-resistant S. aureus, VRSA, VISA, and MRSA. Additionally, the activities of EB and FdUrd exceeded those determined for vancomycin and linezolid. Furthermore, they exhibited strong antimicrobial activity against other important Gram-positive pathogens, including VRE and methicillin-resistant S. epidermidis.

EB, an organoselenium compound, is considered clinically safe but without proven use. It has been widely studied for its anti-inflammatory, anti-atherosclerotic, and antioxidative properties. Independent of its anti-inflammatory effect, EB also has been shown to exhibit antimicrobial activity in vitro. It inhibits the thioredoxin reductase enzyme in Escherichia coli, and it inhibits the antigen 85 (Ag85) complex in Mycobacterium tuberculosis. However, clinical applications and the underlying mechanism of action for its antibacterial activity against S. aureus still remain unclear. In this study, we have established that treatment with EB orally, but not IP, significantly increased mice survival (60%) in a lethal model of septicemic MRSA-infection compared to that of control (FIG. 1A). EB is rapidly absorbed from the gastrointestinal tract, and it maintains a plasma concentration of 2.91 mg/L with 30 mg/kg dose (according to increase in selenium concentration in the blood of $0.84 \pm 0.1$ mg/L$^{-1}$), several-fold higher than MIC$_{90}$. Higher doses or multiple doses might be required to achieve 100% protection. Furthermore, the recognized anti-inflammatory response of EB, combined with the potent antimicrobial activity, make it an excellent candidate for topical treatment of MRSA skin infections.

FdUrd is an anticancer drug used to treat colorectal cancers. FdUrd inhibits thymidylate synthase (a key enzyme in DNA synthesis) and acts as a nucleoside analog that impairs the metabolism and structure of nucleic acids. The antimicrobial activity of nucleoside analog against *S. aureus* has been demonstrated in vitro. FdUrd oral and IP treatment significantly enhanced mouse survival in a lethal model of septicemic MRSA-infection by 60% and 100%, respectively, compared to that of control (FIG. 1B). The bioavailability of oral FdUrd is unpredictable, which probably contributed to a lower protection rate compared to an IP route. While FdUrd shows preclinical promise as a medication for the treatment of MRSA infections, the therapeutic dose can be reduced significantly to avoid drug-associated toxicity. The achieved plasma concentration of the drug after receiving a therapeutic dose is estimated to be more than a thousand-folds higher than the required $MIC_{90}$ against MRSA.

Example 3. Bactericidal Activity of Auranofin and Ebselen Against a Range of Gram-Positive Clinical Isolates In this Example, we demonstrated that Auranofin and Ebselen have potent bactericidal activity against drug-resistant *Staphylococcus* isolates, including methicillin-resistant *Staphylococcus aureus* (MRSA), vancomycin-intermediate *S. aureus* (VISA), vancomycin-resistant *S. aureus* (VRSA) and linezolid-resistant *S. aureus*. Furthermore, they exhibited strong antimicrobial activity against other important Gram-positive pathogens, including vancomycin-resistant *enterococcus* (VRE), *Streptococcus pneumonia*, methicillin-resistant *S. epidermidis*, and *Bacillus anthracis*. The MICs at which 90% of MRSA isolates were inhibited ($MIC_{90s}$) were 0.125 μg/ml and 0.25 μg/ml for Auranofin and Ebselen, respectively (Table 3).

TABLE 3

MIC against a range of Gram +ve clinical isolates

| Clinical isolates (no. of strains) total | MIC (μg/ml) | | | |
|---|---|---|---|---|
| | Auranofin | | Ebselen | |
| 51 clinical isolates | $MIC_{50}$ | $MIC_{50}$ | $MIC_{50}$ | $MIC_{50}$ |
| MRSA (23) | 0.062 | 0.125 | 0.25 | 0.25 |
| VISA and VRSA (14) | 0.062 | 0.062 | 0.125 | 0.25 |
| VRE (14) | 0.125 | 0.125 | 0.5 | 0.5 |

MRSA; methicillin resistant *S. aureus*,
VISA; vancomycin intermediate *S. aureus*,
VRSA; vancomycin resistant *S. aureus*,
VRE; vancomycin resistant *enterococcus*

MICs of Auranofin and Ebselen against G+ve pathogens are several fold lower than the clinically achievable blood concentration of the drugs of 2.37 μg/ml for Auranofin and 2.91 μg/ml for Ebselen. We are using the guidelines of the Clinical and Laboratory Standards Institute (CLSI) to identify MICs.

Example 4. Bactericidal Activity of Auranofin and Ebselen Against a Range of Gram Negative Clinical Isolates In this Example, we showed that Auranofin and Ebselen demonstrated bactericidal activity, in a clinical range, against G −ve pathogens, including metallo-β-Lactamase (NDM-1), carbapenemase (KPC) resistant *K. pneumonia*, and colistin-resistant *P. aeruginosa* isolates from colistin-treated cystic fibrosis patients, when the intrinsic resistance mechanism conferred by the outer membrane (OM) had been artificially compromised (Table 4) by sub-inhibitory concentrations of polymyxin B nonapeptide or colistin (nano molar range that did not inhibit growth of the bacteria). This study indicates that the targets of Auranofin and Ebselen are present in G −ve bacteria and it can be combined, in a clinical range, with other approved drugs that cause leakage in the OM to sensitize G −ve pathogens. MICs of Auranofin and Ebselen against G-ve pathogens are several fold lower than the clinically achievable blood concentration of the drugs of 2.37 μg/ml for Auranofin and 2.91 μg/ml for Ebselen.

TABLE 4

MIC of auranofin and ebselen against G-ve with and without colistin

| Bacteria (49 clinical isolates tested) | MICs of colistin (μg/ml) | Sub-inhibitory conc. of colistin used (μg/ml) | Auranofin (μg/ml) colistin | | Ebselen (μg/ml) colistin | |
|---|---|---|---|---|---|---|
| | | | (−) | (+) | (−) | (+) |
| *A. baumannii* | 0.25 | 0.0625 | 16 | 0.25 | 16 | 0.25 |
| *E.. coli* O157:H7 | 0.25 | 0.0625 | 64 | 0.0625 | 32 | 0.125 |
| *S. Typhimurium* | 1 | 0.25 | 128 | 0.0625 | 32 | 0.0625 |
| *K. pneumonia* | 0.25 | 0.125 | 256 | 0.125 | 64 | 0.0625 |
| *P. aeruginosa* | 0.5 | 0.25 | 256 | 0.0312 | >256 | 0.125 |
| Colistin resistant clinical isolates of *P. aeruginosa* | 16->128 | 1-8 | >256 | 0.0625 | >256 | 0.125 |

Example 5. Auranofin and Ebselen Significantly Reduced *S. aureus* and *S. epidermidis* Biofilm In this Example, we showed that Auranofin and Ebselen can reduce biofilm formation by selective bacterium.

Figure 2:
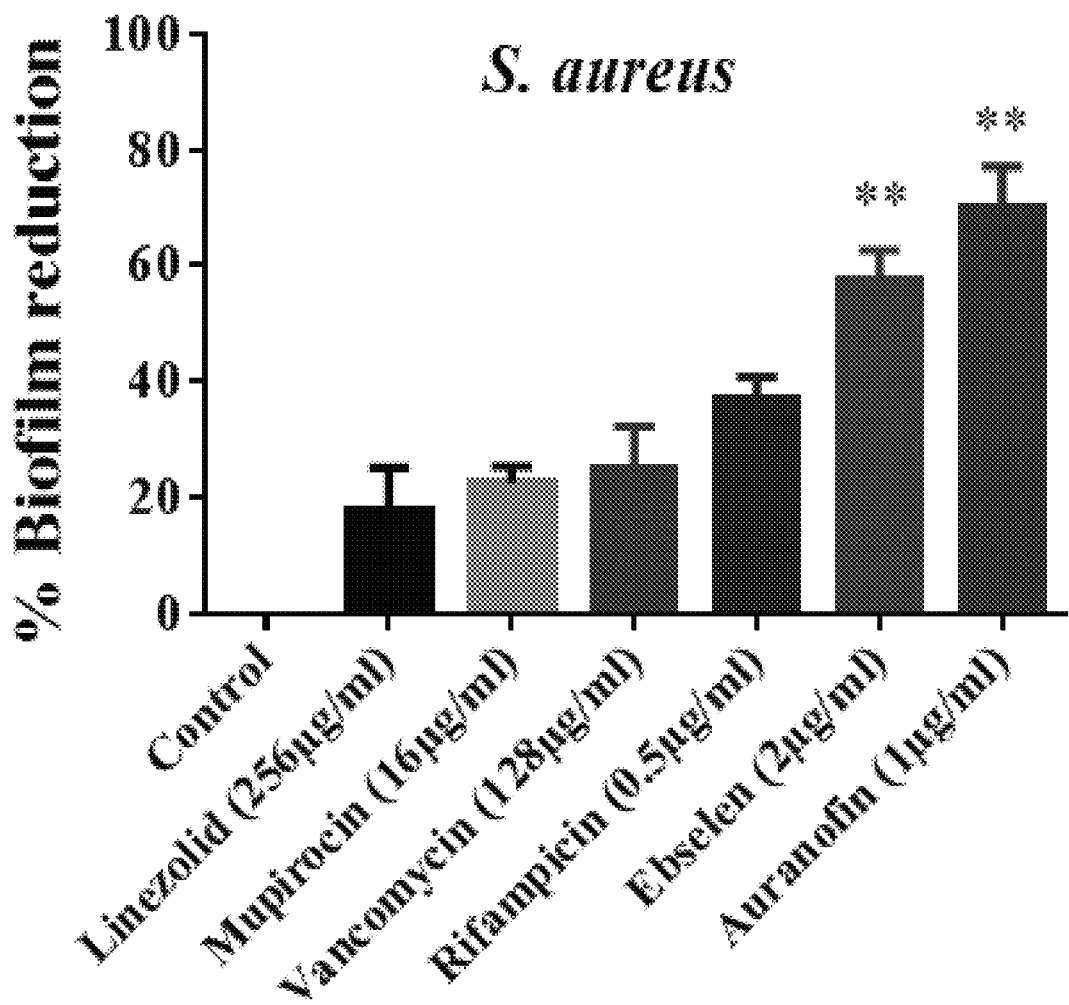
FIG. 2 shows Auranofin and ebselen quantification reduction of *S. aureus* and *S. epidermidis* biofilm. Auranofin and ebselen were superior in reducing adherent biofilms of both *S. aureus* and *S. epidermidis* when compared to conventional antibiotics (linezolid 256 µg/ml (128×MIC), mupirocin 16 µg/ml (128×MIC), vancomycin 128 µg/ml (128×MIC), and rifampicin 0.5 µg/ml (16×MIC). Values are the mean of triplicate samples±SD. (*) Significant from control and antibiotics.

Biofilms are a major contributing factor to lack of healing of chronic wounds, as the matrix-embedded bacteria are recalcitrant to antibiotics and host immune response, rendering them extremely challenging and costly to treat. Auranofin and Ebselen were superior in reducing adherent biofilms of both *S. aureus* and *S. epidermidis* when compared to conventional antibiotics (linezolid 256 μg/ml (128× MIC), mupirocin 16 μg/ml (128×MIC), vancomycin 128 μg/ml (128×MIC), and rifampicin 0.5 μg/ml (16×MIC) (FIG. 2)

Example 6. Topical Auranofin and Ebselen Prove Superior to Conventional Antimicrobials in MRSA Skin Infection In this Example, we compared Auranofin and Ebselen with other conventional antimicrobials in MRSA skin infection and concluded that these two drugs are superior to other available conventional drugs.

Figure 3:
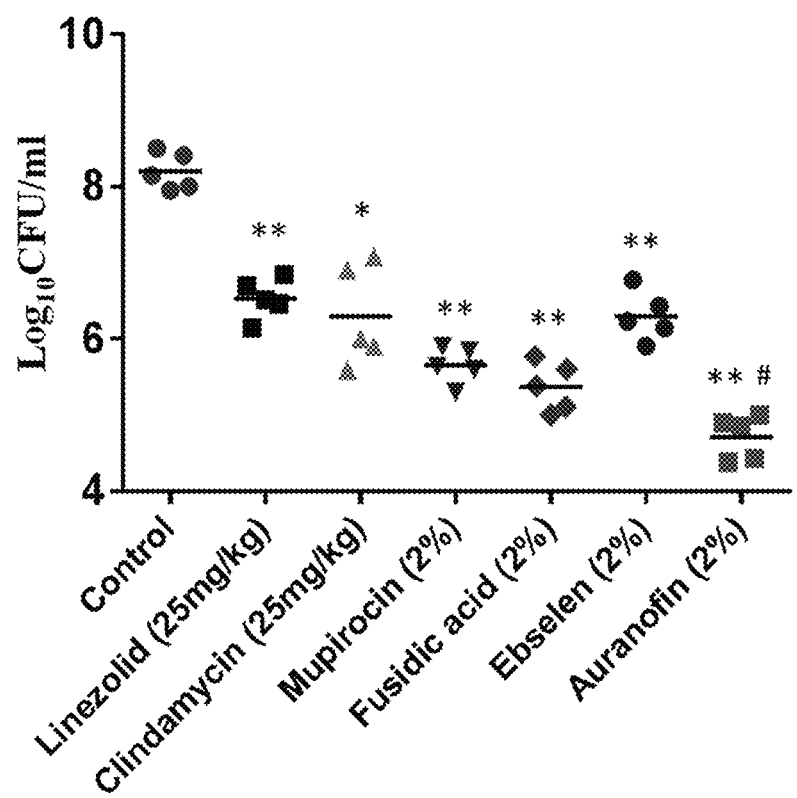
FIG. 3 shows treatment of MRSA skin lesions in mice with ebselen, Auranofin, linezolid, mupirocin, clindamycin, and fusidic acid twice daily for 5 days. Auranofin and ebselen were evaluated in a mouse-model of staphylococcal skin infection. Seven groups of BALB/c mice (n=5) were inoculated with MRSA USA300 ($4.3 \times 10^9$ CFU/ml) intradermally. 48 hours after infection and formation of open wound, four groups were treated topically with 20 mg of 2% Ebselen, 2% Auranofin, 2% mupirocin or 2% fluidic acid in petroleum jelly (ointment—skin protectant). Two groups were treated orally with either linezolid or clindamycin (25 mg/kg). The last group received the vehicles alone (petroleum jelly). All groups were treated twice a day for 5 days. Auranofin and Ebselen significantly reduced the bacterial load and auranofin was superior to traditional antimicrobial agents currently utilized for topical treatment.

Since the clinical severity of bacterial skin infections is driven by the excess host pro-inflammatory cytokines rather than by bacterial burden, the recognized anti-inflammatory response of Auranofin and Ebselen combined with the potent antimicrobial, killing intracellular MRSA, and antibiofilm activities, should provide great advantage in the treatment of bacterial skin infection and wound healing. In this Example, we evaluated Auranofin and Ebselen in a mouse-model of staphylococcal skin infection. Seven groups of BALB/c mice (n=5) were inoculated with MRSA USA300 ($4.3\times10^9$ CFU/ml) intradermally. 48 hours after infection and formation of open wound, four groups were treated topically with 20 mg of 2% ebselen, 2% auranofin, 2% mupirocin or 2% fluidic acid in petroleum jelly (ointment—skin protectant). Two groups were treated orally with either linezolid or clindamycin (25 mg/kg). The last group received the vehicles alone (petroleum jelly). All groups were treated twice a day for 5 days. Auranofin and Ebselen significantly reduced the bacterial load and Auranofin was superior to traditional antimicrobial agents currently utilized for topical treatment (FIG. 3).

Figure 4:
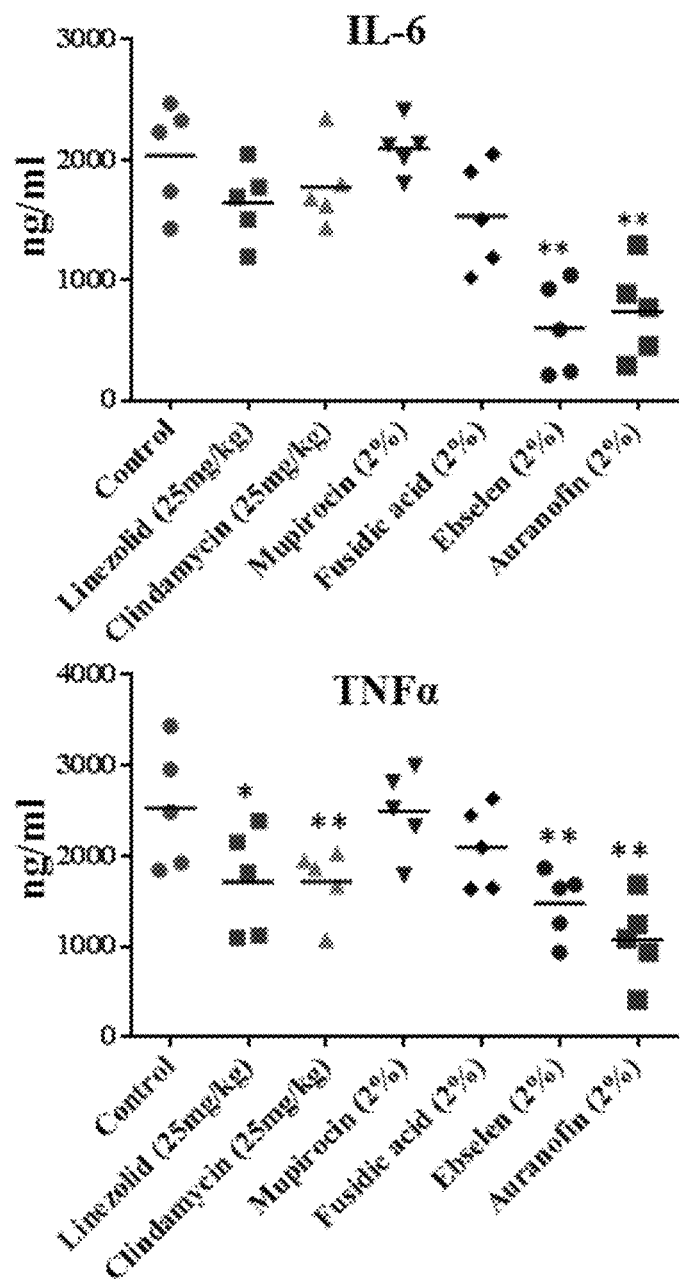
FIG. 4 shows Effect of Ebselen and Auranofin on cytokines production. Each points represents single mice and each group has 5 mice. P values of (*$P \le 0.05$) (**$P \le 0.01$) are considered as significant. We investigated the immunomodulatory activity of Auranofin and ebselen in a topical application against MRSA skin infection in mice. Auranofin and Ebselen significantly reduced the levels of the pro-inflammatory cytokines tumor necrosis factor-α (TNF-α), interleukin-6 (IL-6).

Example 7 Auranofin and Ebselen Reduce Inflammatory Cytokines Induced by MRSA Skin Infection In this Example, we investigated the immunomodulatory activity of Auranofin and Ebselen in a topical application against MRSA skin infection in mice. Auranofin and Ebselen significantly reduced the levels of the pro-inflammatory cytokines tumor necrosis factor-$\alpha$ (TNF-$\alpha$), interleukin-6 (IL-6), interleukin-1 beta (IL-1$\beta$), and monocyte chemo attractant protein-1 (MCP-1) (FIG. 4 and data not shown for IL-1$\beta$ or MCP-1). These cytokines are thought to play a greater role in the severity of *S. aureus* skin infections more than the size of the bacterial burden and can lead to an infection persisting for a longer time period. Therefore, the ability of Auranofin and Ebselen reduces the production of these cytokines in the infected mice, indicating the clinical relevance of these drugs if used for antimicrobial treatment.

Example 8. Auranofin and Ebselen Kill Intracellular MRSA

Figure 5:
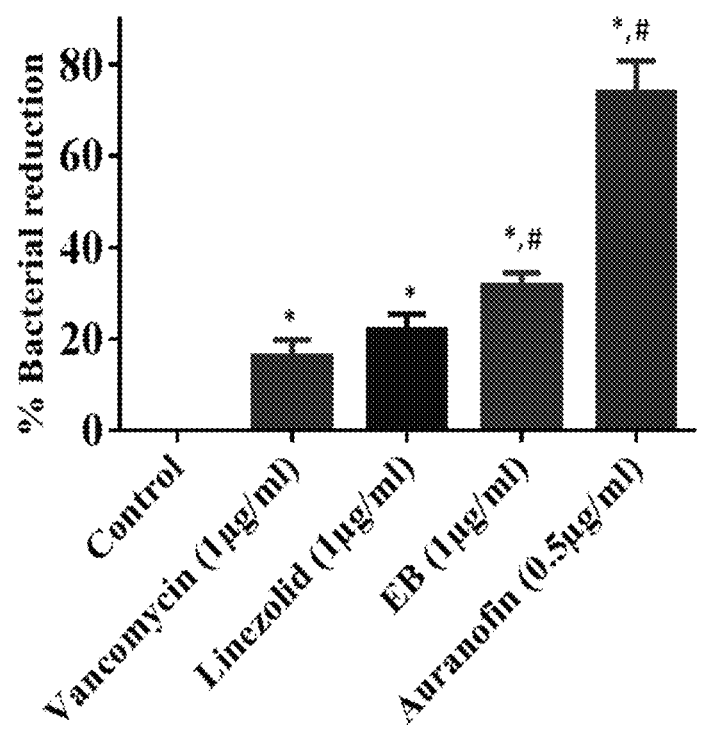
FIG. 5 shows activity of Auranofin, Ebselen, vancomycin and linezolid against intracellular MRSA USA300 in J774A.1 cells. Treatment with Auranofin and Ebselen was superior in reducing intracellular MRSA when compared to conventional antibiotics (vancomycin and linezolid).

In this Example we investigated if Auranofin and Ebselen possess intracellular anti-staphylococcal activity. FIG. 5 shows that treatment with Auranofin and Ebselen was superior in reducing intracellular MRSA when compared to conventional antibiotics (vancomycin and linezolid) in J774A.1 cells.

Some extracellular pathogens such as *S. aureus* are also capable of invading and surviving within the mammalian host cells. Survival of *S. aureus* within host cells may provide a reservoir relatively protected from antibiotics, thus enabling long-term colonization of the host and explaining clinical failures and relapses after antibiotic therapy. Moreover, treatment of intracellular stage with antimicrobials is very challenging because most antibiotics do not actively pass through cellular membranes. Therefore, clinical failures of drug of choice, such as vancomycin, to cure *S. aureus* pneumonia have exceeded 40% and have been attributed mainly to poor intracellular penetration of the drug and consequently to the failure to kill intracellular MRSA in alveolar macrophages. In addition, intracellular persistence of *S. aureus* constitutes a potent virulence components for various skin diseases such as impetigo and folliculitis. Hence, finding antimicrobials that possess both extra- and intracellular activity would be an optimum strategy to treat such invasive intracellular *S. aureus* infections. Auranofin and Ebselen fulfill such optimization treatment of invasive intracellular *S. aureus* infections.

Example 9. Auranofin and Ebselen Inhibit MRSA Toxin Production

In this Example we tested whether the inhibition of protein synthesis by Auranofin and Ebselen lead to inhibition of virulence factors and toxin production in MRSA. Antimicrobials that suppress translation in *S. aureus* markedly suppress expression of virulence factors and the formation of toxins such as $\alpha$-hemolysin (hla), toxic shock syndrome toxin-1 (TSST-1), and Panton-Valentine leucocidin (PVL) that will lead to better treatment outcomes.

Figure 6:
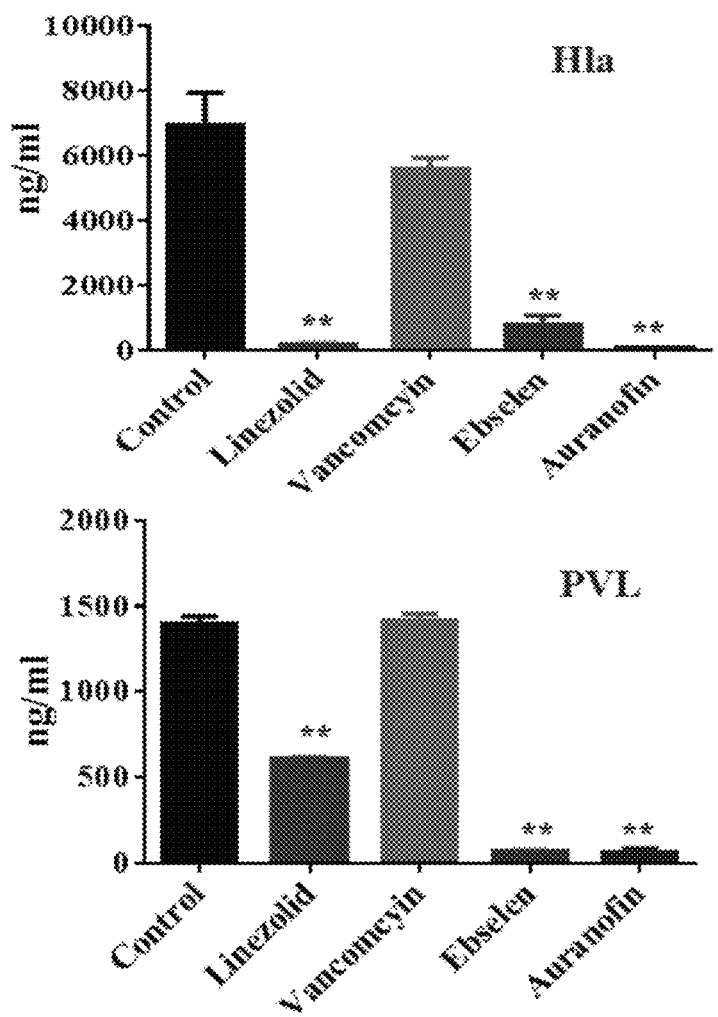
FIG. 6 shows inhibition of protein synthesis by Auranofin and Ebselen leads to inhibition of virulence factors and toxin production in MRSA. The effect of Auranofin and Ebselen after 1 hour incubation with MRSA USA300-0114 on production of these important toxins hla and PVL by ELISA shows Auranofin and Ebselen significantly suppressed toxin production in MRSA.

We tested the effect of Auranofin and Ebselen after 1 hour incubation with MRSA USA300-0114 on production of these important toxins hla and PVL by ELISA and found that Auranofin and Ebselen significantly suppressed toxin production in MRSA (FIG. 6).

Example 10. Effect on Mitochondrial Biogenesis

In this Example we showed that Auranofin and Ebselen do not affect mitochondria protein synthesis.

Figure 7:
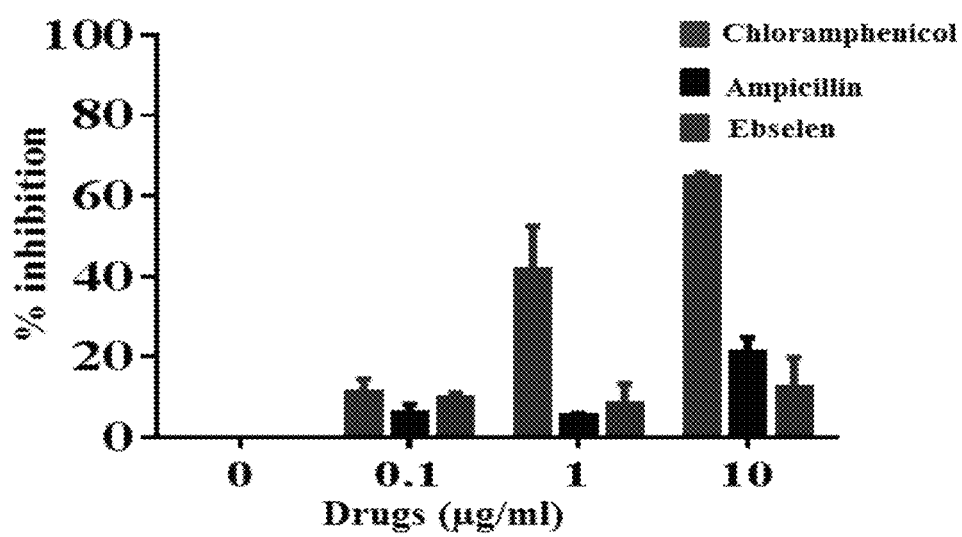
FIG. 7 shows the effect of Ebselen on mitochondrial protein synthesis directly within the mammalian cells. In-cell ELISA was performed in J774A.1 cells treated with Ebselen, and control antimicrobials (chloramphenicol and ampicillin) for three days to detect the levels of two proteins (subunit I of Complex IV (COX-I), which is mitochondrial DNA (mtDNA)-encoded, and the 70 kDa subunit of Complex II (SDH-A), which is nuclear DNA (nDNA)-encoded. Ebselen had no significant inhibition (less than 10%) of mitobiogenesis, similar to the effect of ampicillin, which does not interfere with mitochondrial protein synthesis process.

Due to concern about the possible mitochondrial toxicities associated with many antibacterial protein synthesis inhibitors such as linezolid and chloramphenicol, we tested the effect of Auranofin and Ebselen on mitochondrial protein synthesis directly within the mammalian cells. In-cell ELISA was performed in J774A.1 cells treated with Auranofin, ebselen, and control antimicrobials (chloramphenicol and ampicillin) for three days to detect the levels of two proteins (subunit I of Complex IV (COX-I), which is mitochondrial DNA (mtDNA)-encoded, and the 70 kDa subunit of Complex II (SDH-A), which is nuclear DNA (nDNA)-encoded. Ebselen and Auranofin had no significant inhibition (less than 10%) of mitobiogenesis, similar to the effect of ampicillin, which does not interfere with mitochondrial protein synthesis process (FIG. 7) (only Ebselen data shown). These results provide valuable information about these drugs safety profile and the lack of interference with mammalian protein synthesis and mitobiogenesis.

Example 11. Synergistic Activities of Auranofin and Ebselen with Conventional Antibiotics In Vitro and in Cell Culture In this Example we showed that Auanofin and Ebselen may be combined with conventional antibiotics to achieve synergistic effect.

With the rapid emergence of multidrug-resistant strains, monotherapy with single antibiotic has become less effective. Therefore, alternative strategies such as combinational therapy have been used in the healthcare setting to improve the morbidity associated with MRSA infections and to reduce the likelihood of emergence of resistant strains. To ascertain whether Auranofin and Ebselen have the potential to be combined with conventional antimicrobials such as linezolid, clindamycin, vancomycin, ciprofloxacin, erythromycin, rifampicin, gentamicin, mupirocin, fusidic acid, retapamulin and daptomycin against multiple MRSA and VRSA strains, we evaluated the synergistic activity in in-vitro and in infected cell culture assay. Auranofin and Ebselen were found to exhibit a synergistic relationship with most of the tested conventional antimicrobials in vitro against all tested strains (with few exceptions such as VRSA5 strain) (data not shown but available). In infected cell cultures, clindamycin, erythromycin, and rifampicin showed synergistic activity when combined with Auranofin and Ebselen and significantly reduced intracellular MRSA when compared to monotherapy. Identifying antibiotics that can be synergistically paired with Auranofin and Ebselen can potentially prolong the clinical utility of these antibiotics, reduce the likelihood of emergence of resistant strains, and supplement current therapies.

Example 12. Killing of Persister Cells by Antibiotics and Auranofin

In this Example, we showed that Auranofin can be combined with other antibiotics to treat persister *S. aureus*.

Figure 8:
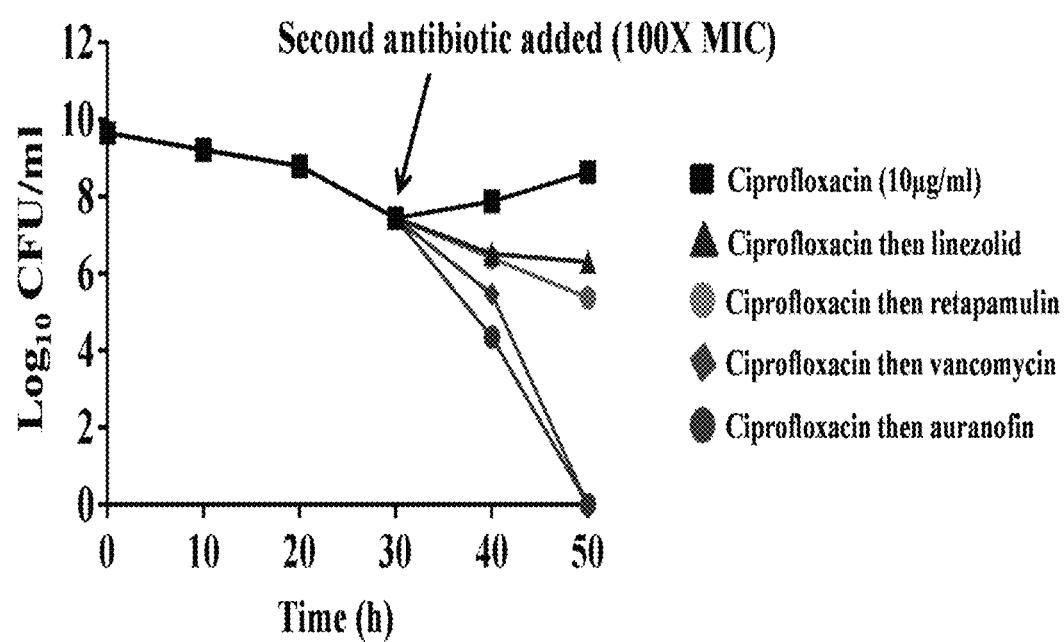
FIG. 8 shows effect of Auranofin on *S. aureus* persister cells. Auranofin and Ebselen were found to exhibit a synergistic relationship with most of the tested conventional antimicrobials in vitro against all tested strains. In infected cell cultures, clindamycin, erythromycin, and rifampicin showed synergistic activity when combined with Auranofin and Ebselen and significantly reduced intracellular MRSA when compared to monotherapy. Identifying antibiotics that can be synergistically paired with Auranofin and Ebselen can potentially prolong the clinical utility of these antibiotics, reduce the likelihood of emergence of resistant strains, and supplement current therapies. The effect of Auranofin and conventional antibiotics (linezolid, retapamulin and vancomycin) on *S. aureus* persister cells that demonstrated tolerance to ciprofloxacin was investigated. When treated with ciprofloxacin, MRSA USA300 in exponential growth phase produces a biphasic killing pattern that results in surviving persister cells. Subsequent addition of conventional antimicrobials such as linezolid and retapamulin had minimal impact in reducing the number of planktonic persisters. However, treatment with auranofin resulted in complete eradication of planktonic persister cells after 48 h, a result that is comparable with vancomycin.

Persister *S. aureus*, bacteria that presumably enter a dormant state to survive antibiotic treatment, are very challenging to target. Moreover, no treatment strategy has been established, despite the high mortality associated with persistent MRSA infections. The effect of Auranofin and conventional antibiotics (linezolid, retapamulin and vancomycin) on *S. aureus* persister cells that demonstrated tolerance to ciprofloxacin was investigated as described previously in this Example. When treated with ciprofloxacin, MRSA USA300 in exponential growth phase produces a biphasic killing pattern that results in surviving persister cells (FIG. 8). Subsequent addition of conventional antimicrobials such as linezolid and retapamulin had minimal impact in reducing the number of planktonic persisters. However, treatment with Auranofin resulted in complete eradication of planktonic persister cells after 48 h, a result that is comparable with vancomycin (FIG. 8)

Example 13. In Vivo Proof-of-Principle Experiments

Figure 9:
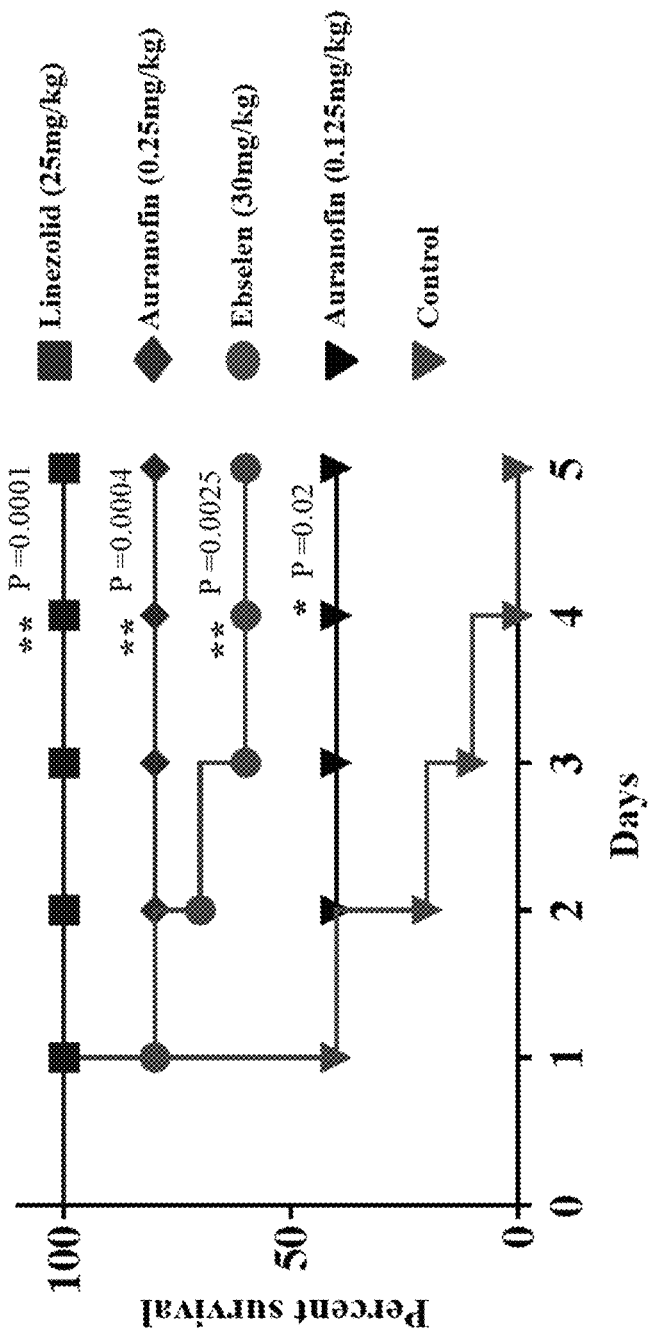
FIG. 9 shows mouse model of MRSA systemic infection with repurposing two FDA approved drugs systemically. For MRSA systemic infection, neutropenic Female BALB/c mice were inoculated IP with $1 \times 10^9$ MRSA USA300. At 1 h after infection, the mice were divided into five groups (n=10 per group) and four groups were treated orally with linezolid 25 mg/kg, Auranofin 0.125 and 0.25 mg/kg (dose approved for treatment of juvenile rheumatoid arthritis in children and Ebselen 30 mg/kg. One group was used as a control with no treatment. Treatment was continued once daily for two more days. All drugs significantly increased mice survival (60% Ebselen, 40% and 80% oral Auranofin) compared to that of control.
Figure 10:
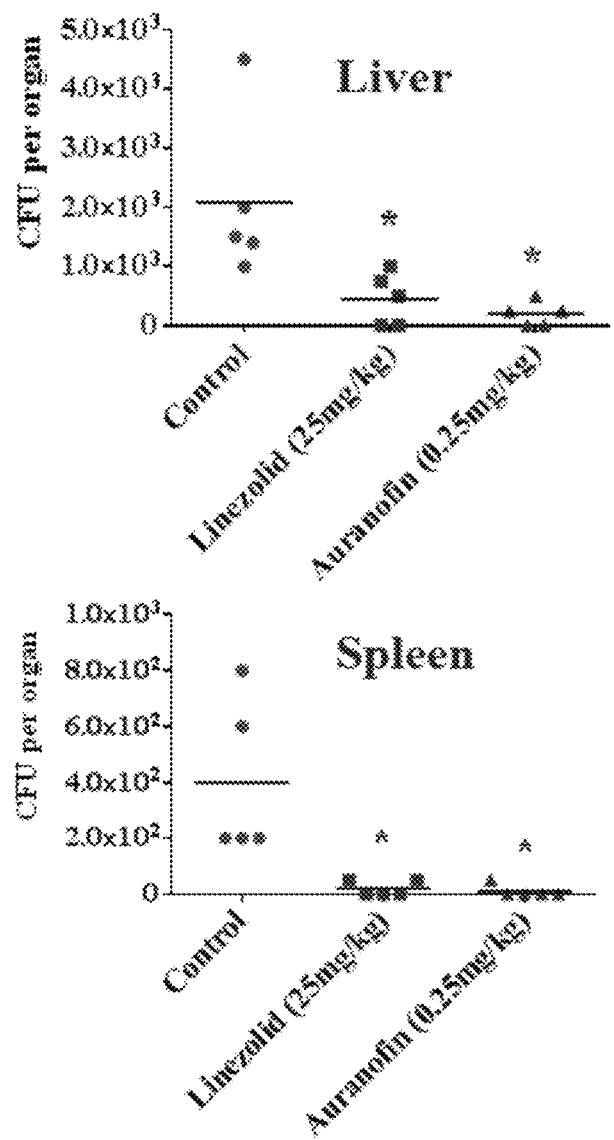
FIG. 10 shows a non-lethal MRSA infection mice model ($2 \times 10^7$ CFU MRSA USA300 IP), two doses of oral Auranofin (0.25 mg/kg) significantly reduced the bacterial load in the liver and spleen, comparable to linezolid (25 mg/kg).

In this Example, in view of our results demonstrating potent antimicrobial in-vitro and in MRSA skin infection (above), we moved forward with a preliminary in-vivo experiment in a mouse model of MRSA systemic infection to ensure the feasibility of repurposing these two drugs systemically. For MRSA systemic infection, neutropenic Female BALB/c mice were inoculated IP with $1 \times 10^9$ MRSA USA300. At 1 h after infection, the mice were divided into five groups (n=10 per group) and four groups were treated orally with linezolid 25 mg/kg, auranofin 0.125 and 0.25 mg/kg (dose approved for treatment of juvenile rheumatoid arthritis in children (68-70) and ebselen 30 mg/kg. One group was used as a control with no treatment. Treatment was continued once daily for two more days. All drugs significantly increased mice survival (60% ebselen, 40% and 80% oral auranofin) compared to that of control (FIG. 9). In a non-lethal MRSA infection mice model ($2 \times 10^7$ CFU MRSA USA300 IP), two doses of oral auranofin (0.25 mg/kg) significantly reduced the bacterial load in the liver and spleen, comparable to linezolid (25 mg/kg) (FIG. 10).

Example 14. Macromolecular Synthesis (MMS)

Figure 11:
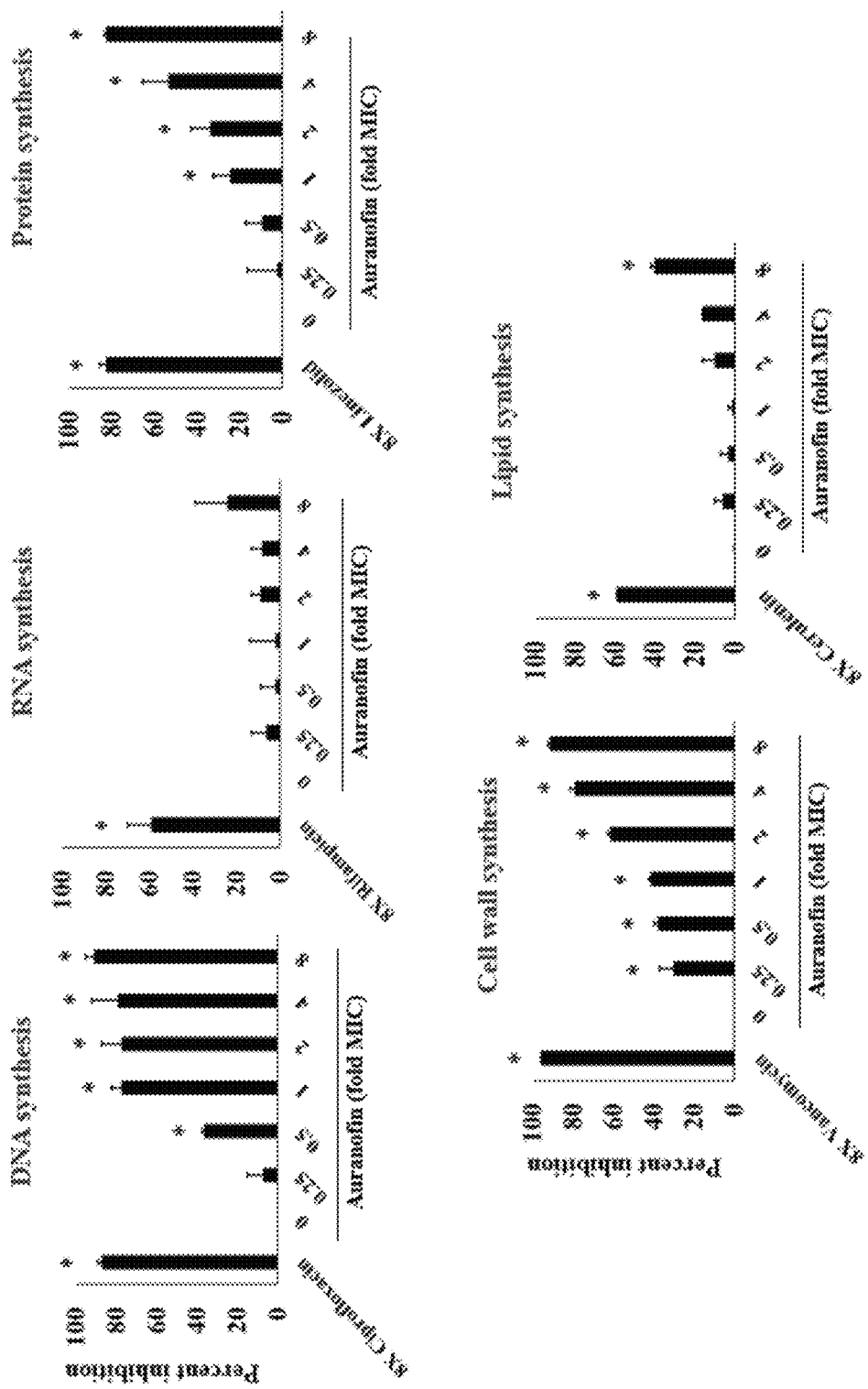
FIG. 11 shows the dose response effect of Auranofin and Ebselen on incorporation of radioactive precursors into macromolecules in *S. aureus*. For Auranofin: DNA, protein and cell wall synthesis inhibition were detected with a clear dose-dependent disruption at concentrations significantly below the MIC (0.25). Whereas no significant effect was observed on the lipid and RNA synthesis up to 4×MIC.

In this Example we examined the effect of Auranofin and Ebselen on incorporation of radioactive precursors into macromolecules in *S. aureus*. For Auranofin: DNA, protein and cell wall synthesis inhibition were detected with a clear dose-dependent disruption at concentrations significantly below the MIC (0.25). Whereas no significant effect was observed on the lipid and RNA synthesis up to 4×MIC (dose response FIG. 11). Ebselen primarily inhibited DNA and protein synthesis at 1× the MIC (Data not shown but available).

Example 15. Auranofin and Ebselen Inhibit Bacterial Protein Synthesis

Figure 12:
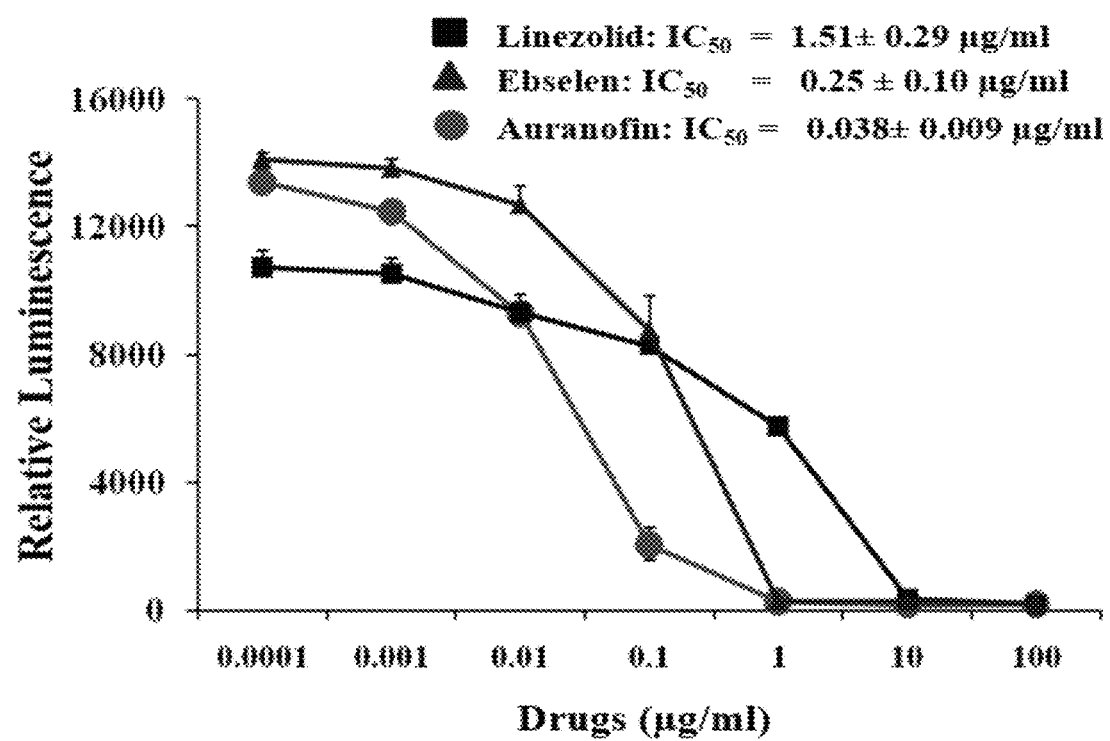
FIG. 12 shows effects of Auranofin and Ebselen on bacterial, mammalian and mitochondrial protein-synthesis. For bacterial protein-synthesis inhibition, *E. coli* cellular extracts in a transcription and translation assay were used to monitor protein production via luciferase readout. Auranofin and Ebselen strongly inhibited bacterial translation process. Auranofin and Ebselen, exhibited $IC_{50}$ of 0.038 μg/ml and 0.25 μg/ml, respectively.
Figure 13:
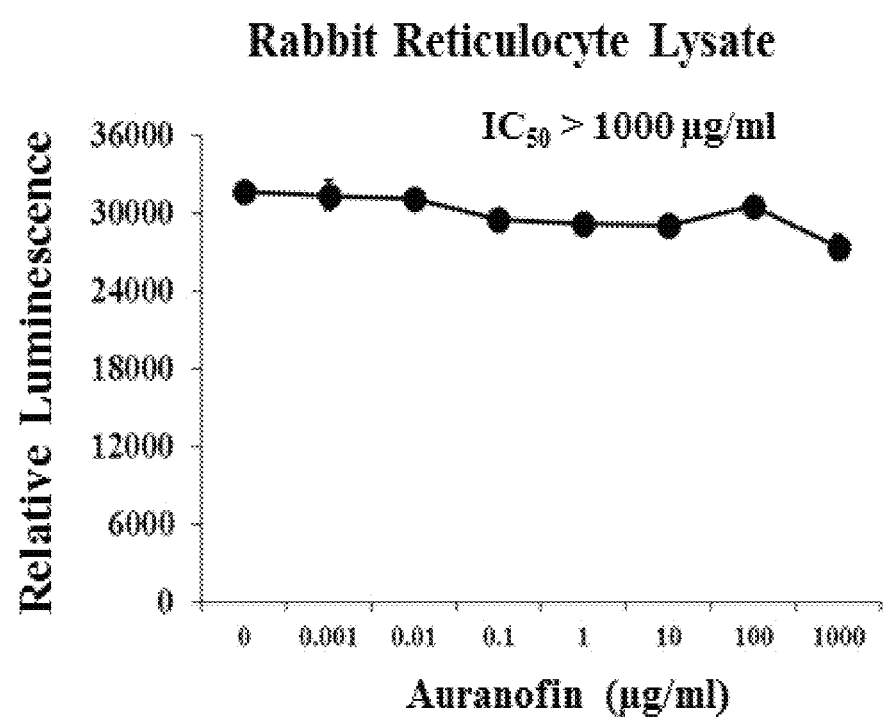
FIG. 13 shows Auranofin did not inhibit translation in mammalian protein synthesis in a rabbit reticulocyte lysate system. ($IC_{50}$) of Auranofin in rabbit reticulocyte extract. The data shows average luciferase readout of protein production from two independent experiments. The results are given as means±SD (data without error bars indicate that the SD is too small to be seen).

In this Example, we tested the effects of the two drugs on bacterial, mammalian and mitochondrial protein-synthesis. For bacterial protein-synthesis inhibition, we used *E. coli* cellular extracts in a transcription and translation assay that monitors protein production via luciferase readout. As expected from MMS and proteomics results, Auranofin and Ebselen strongly inhibited bacterial translation process (FIG. 12). Auranofin and Ebselen, exhibited $IC_{50}$ of 0.038 µg/ml and 0.25 µg/ml, respectively. These results confirm MMS and proteomics results and indicate that both drugs act by a favorable mechanism of action and inhibit bacterial protein synthesis and inhibit toxin production. Both drugs did not inhibit translation in mammalian protein synthesis in a rabbit reticulocyte lysate system (FIG. 13) or Mitobiogenesis (above)

Those skilled in the art will recognize that numerous modifications can be made to the specific implementations described above. The implementations should not be limited to the particular limitations described. Other implementations may be possible.

The invention claimed is:

1. A method of using a pre-existing FDA approved non-antibiotic drug to treat a patient infected with multi-drug resistance bacterium, comprising:
   screening a library, wherein the library contains a plurality of FDA approved drugs and small molecules, against ESKAPE pathogens (*Enterococcus faecium, Staphylococcus aureus, Klebsiella pneumoniae, Acinetobacter baumannii, Pseudomonas aeruginosa,* and *Enterobacter cloacae*);
   identifying Ebselen, Auranofin and 5-fluoro-2'-deoxyuridine (FdUrd) for their ability to reduce biofilm mass, regulate exotoxin production associated inflammatory cascade, perform intracellular bacteria killing, and protect systematic skin infection in mouse model without interfering mitochondrial protein synthesis and macromolecular synthesis in said ESKAPE pathogen infected host s to confirm their potent antimicrobial activity in an applicable clinical range of about sub-micromolar to about nanomolar concentration against a plurality of pathogens;
   applying Ebselen, Auranofin or 5-fluoro-2'-deoxyuridine (FdUrd) in said applicable clinical range to the patient and wherein the application of said drugs reduces the levels of the pro-inflammatory cytokines tumor necrosis factor-α (TNF-α), interleukin-6 (IL-6), interleukin-1 beta (IL-1β), and monocyte chemo attractant protein-1(MCP-1) in the patient.

2. The method according to claim 1, wherein said pathogens are selected from the group consisting of methicillin-resistant *Staphylococcus aureus* (MRSA), vancomycin-resistant *S. aureus* (VRSA), *Streptococcus pneumoniae,* vancomycin-resistant *enterococcus* (VRE), and vancomycin-intermediate *S. aureus* (VISA).

3. The method according to claim 1, wherein said pathogens are selected from the group consisting of metallo-β-Lactamase (NDM-1), carbapenemase (KPC) resistant *K. pneumonia,* and colistin-resistant *P. aeruginosa*.

4. A method of using Ebselen, Auranofin or 5-fluoro-2'-deoxyuridine (FdUrd) for treating multi-drug resistant bacteria infection, comprising identifying a patient infected with multi-drug resistant bacteria; applying to said patient a clinical relevant dosage of Ebselen, Auranofin or 5-fluoro-2'-deoxyuridine (FdUrd), wherein said clinical relevant dosage is the minimum concentration at which 90% of said multi-drug resistant bacteria growth is inhibited (MIC90), the application of said drugs is through oral for Ebselen, and through oral or IP injection for Auranofin or 5-fluoro-2'-deoxyuridine (FdUrd), and wherein the application of said drugs reduces the levels of the pro-inflammatory cytokines tumor necrosis factor-α (TNF-α), interleukin-6 (IL-6), interleukin-1 beta (IL-1β), and monocyte chemo attractant protein-1(MCP-1) in the patient.

5. The method according to claim 4, wherein said multi-drug resistant bacteria are gram-positive pathogens selected from the group consisting of methicillin-resistant *Staphylococcus aureus* (MRSA), vancomycin-resistant *S. aureus* (VRSA), *Streptococcus pneumoniae*, vancomycin-resistant *enterococcus* (VRE), and vancomycin-intermediate *S. aureus* (VISA).

6. The method according to claim 4, wherein said multi-drug resistant bacteria are gram-negative pathogens selected from the group consisting of metallo-β-Lactamase (NDM-1), carbapenemase (KPC) resistant *K. pneumonia*, and colistin-resistant *P. aeruginosa*.

7. A combinational therapy to treat a patient with bacterial infection to control the development of drug-resistance, comprising applying a clinical range of the non-antibiotic drug selected from the group consisting of Ebselen, and 5-fluoro-2'-deoxyuridine (FdUrd), with a conventional antibiotic drug selected from the group consisting of linezolid, clindamycin, vancomycin, ciprofloxacin, erythromycin, rifampicin, gentamicin, mupirocin, fusidic acid, retapamulin and daptomycin to the patient, wherein the combination of said non-antibiotic drug and said conventional antibiotic drug at a minimum concentration of achieving 90% bacterial growth inhibition.

8. The combinational therapy according to claim 7, wherein said non-antibiotic drug provides synergy to said conventional antibiotic drug.

9. A method of treating intracellular bacterial infection in a patient comprising applying a clinical range of about sub-micromolar to about nanomolar concentration of the non-antibiotic drug selected from the group consisting of Ebselen, Auranofin and 5-fluoro-2'-deoxyuridine (FdUrd) until the expression of virulence factors and the formation of toxins is suppressed, wherein said virulent factors and toxins are selected from the group consisting of α-hemolysin (hla), toxic shock syndrome toxin-1 (TSST-1), and Panton-Valentine leucocidin (PVL) and wherein the application of said drugs reduces the levels of the pro-inflammatory cytokines tumor necrosis factor-α (TNF-α), interleukin-6 (IL-6), interleukin-1 beta (IL-1β), and monocyte chemo attractant protein-1 (MCP-1) in the patient.

10. The method according to claim 4, wherein said multidrug resistant bacteria are gram-positive pathogens selected from the group consisting of methicillin-resistant *Staphylococcus aureus* (MRSA), vancomycin-resistant *S. aureus* (VRSA), *Streptococcus pneumoniae*, vancomycin-resistant *enterococcus* (VRE), and vancomycin-intermediate *S. aureus* (VISA).

11. The method according to claim 4, wherein said multidrug resistant bacteria are gram-negative pathogens selected from the group consisting of metallo-β-Lactamase (NDM-1), carbapenemase (KPC) resistant *K. pneumonia*, and colistin-resistant *P. aeruginosa*.

* * * * *